(12) United States Patent
Madela

(10) Patent No.: US 11,840,544 B2
(45) Date of Patent: Dec. 12, 2023

(54) INTERMEDIATES IN THE SYNTHESIS OF C3-SUBSTITUTED CEPHALOSPORINS

(71) Applicant: Norbrook Laboratories Limited, Down (GB)

(72) Inventor: Karolina Madela, Down (GB)

(73) Assignee: Norbrook Laboratories Limited, Down (GB)

( * ) Notice: Subject to any disclaimer, the term of this patent is extended or adjusted under 35 U.S.C. 154(b) by 31 days.

(21) Appl. No.: 17/255,371

(22) PCT Filed: Jul. 2, 2019

(86) PCT No.: PCT/GB2019/051871
§ 371 (c)(1),
(2) Date: Dec. 22, 2020

(87) PCT Pub. No.: WO2020/008183
PCT Pub. Date: Jan. 9, 2020

(65) Prior Publication Data
US 2021/0261571 A1 Aug. 26, 2021

(30) Foreign Application Priority Data

Jul. 2, 2018 (GB) .................................... 1810849

(51) Int. Cl.
*C07D 501/10* (2006.01)
*C07D 307/16* (2006.01)

(52) U.S. Cl.
CPC ......... *C07D 501/10* (2013.01); *C07D 307/16* (2013.01)

(58) Field of Classification Search
None
See application file for complete search history.

(56) References Cited

U.S. PATENT DOCUMENTS 4,518,528 A 5/1985 Rasnick

FOREIGN PATENT DOCUMENTS

| EP | 1803715 A1 | 7/2007 |
|---|---|---|
| WO | WO 92/01696 A1 | 2/1992 |
| WO | WO 2010/117796 A2 | 10/2010 |

OTHER PUBLICATIONS

Goldberg FW, "Optimization of Brain Penetrant 11β-Hydroxysteroid Dehydrogenase Type I Inhibitors and in Vivo Testing in Diet-Induced Obese Mice", Journal of Medicinal Chemistry, vol. 57, No. 3, 2014, pp. 970-986.
Bateson JH, et al, "Novel C-3 Cyclic Ether Cephalosporins and Their Orally Absorbed Prodrug Esters", Journal of Antibiotics, Nature Publishing Group, vol. 47, No. 2, Feb. 1, 1994, pp. 253-256.
De Kimpe, N., et al., "A Convenient Synthesis of 1-Chloro-2-alkanones", Georg Thieme Verlag, Stuttgart, DE, No. 2, Feb. 1, 1987, pp. 188-190.
International Search Report and Written Opinion of PCT/GB2019/051871 dated Jan. 9, 2020; 11 pages.
Great Britain Search Report for patent application No. GB 1810849.8 dated Jan. 30, 2019.

*Primary Examiner* — Po-Chih Chen
(74) *Attorney, Agent, or Firm* — SQUIRE PATTON BOGGS (US)

(57) ABSTRACT

Disclosed herein are novel and inventive methods for preparing intermediates in the synthesis of C3-substituted cephalosporins. One preferred C3-substituted cephalosporin of clinical interest is Cefovecin. Accordingly, the present invention provides for methods of preparing reactive halogen intermediates for use in the synthesis of C3-substituted cephalosporins, such as Cefovecin. In the case of Cefovecin the reactive intermediates are of the formula:

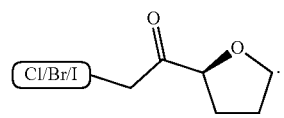

12 Claims, No Drawings

INTERMEDIATES IN THE SYNTHESIS OF C3-SUBSTITUTED CEPHALOSPORINS

This application is a national-stage filing under 37 USC 371(c) of International Application No. PCT/GB2019/051871, filed Jul. 2, 2019, which claims priority to, and the benefit of, Great Britain Patent Application GB1810849.8, filed Jul. 2, 2018.

FIELD OF THE INVENTION

The cephalosporin class of β-lactam antibiotics find clinical relevance in both human and animal medicine. Cefovecin is a notable cephalosporin antibiotic utilised in the field of veterinary medicine. Disclosed herein are novel intermediate compounds utilised in the synthesis Cefovecin, and other C3-substituted cephalosporins.

BACKGROUND TO THE INVENTION

C3-Substituted cephalosporins are attractive targets in the field of medicinal chemistry as the C3-substituent is utilised to modify many properties of the molecule.

Cefovecin Sodium salt (1) is an antibiotic of the cephalosporin class, licensed for the treatment of skin infections in cats and dogs. It is formulated as a single enantiomer for reconstitution in a sterile aqueous diluent, and marketed under the trade name Convenia®. The Cefovecin molecule is disclosed in patent applications WO9201695/WO9201696 to Zoetis/Pfizer, and the final drug product dosage form (Convenia®) is the subject of patent application WO03045435 to Zoetis/Pfizer.

As with all single enantiomer compounds, the synthesis of Cefovecin is complex and challenging. Synthetic processes for the preparation of Cefovecin are disclosed in various patent applications to Pfizer and Zoetis including WO9201695, WO9201696, GB2300856, EP1178049, WO0246199, WO0246198, and WO05092900.

Each of the above patent applications largely focuses on a different aspect of the synthesis of the Cefovecin molecule. However, one of the most critical aspects of the synthesis is the incorporation of an optically active tetrahydrofuran ring into the C3-position of the cephalosporin ring system. The other synthetic transformations, whilst challenging, are largely well known in cephalosporin/penicillin chemistry.

The preferred synthesis of the Cefovecin API starts from the enantiopure, readily available starting material Penicillin G potassium salt (2). This is subjected to a series of standard transformations in penicillin chemistry to generate ring opened intermediate (3), with preserved stereochemistry.

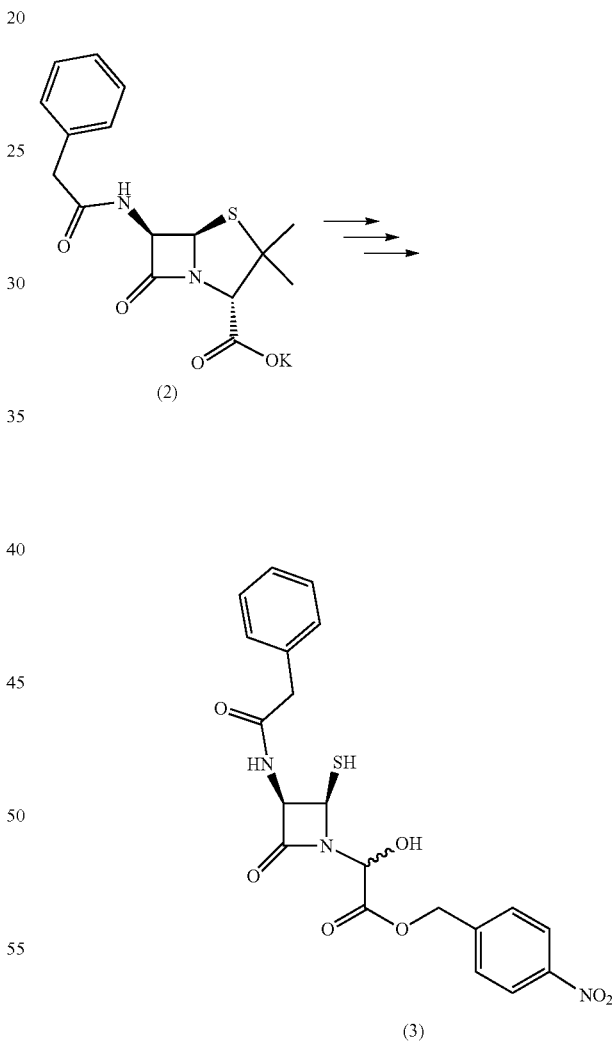

The reactive thiol moiety on intermediate (3) is alkylated with (S)-2-(α-bromoacetyl)-tetrahydrofuran (4b) to introduce an enantiopure furan ring onto thioether intermediate (5).

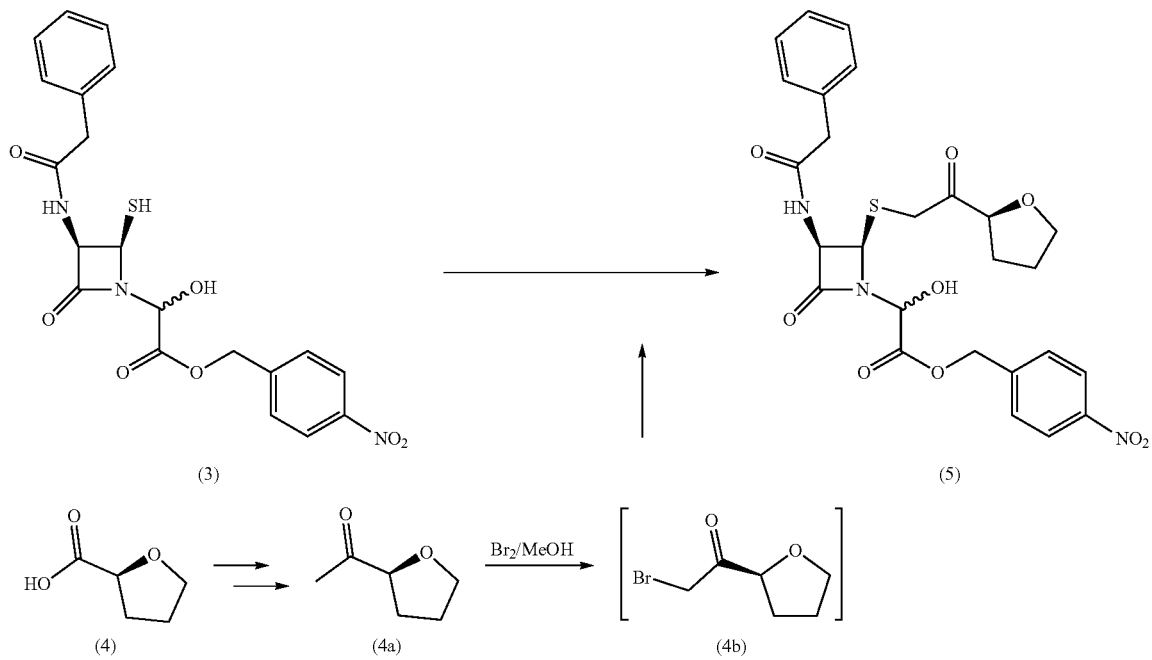

(3) → (5)

(4) → (4a) —Br₂/MeOH→ (4b)

Thioether intermediate (5) is subsequently cyclised utilising Wittig Chemistry to yield a C3-substituted cephalosporin, which undergoes various further standard processing steps to yield Cefovecin sodium salt (1).

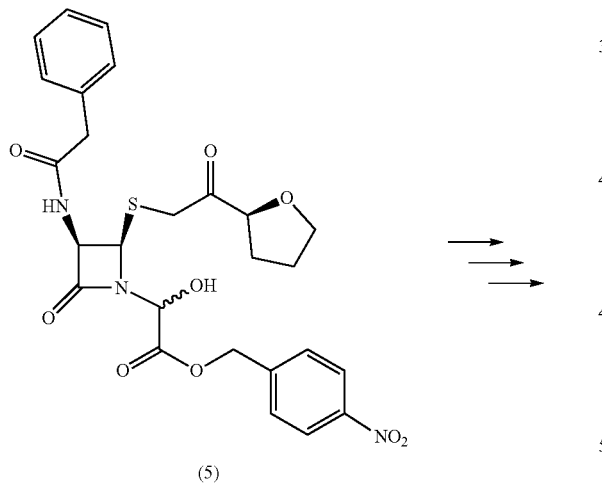

(5)

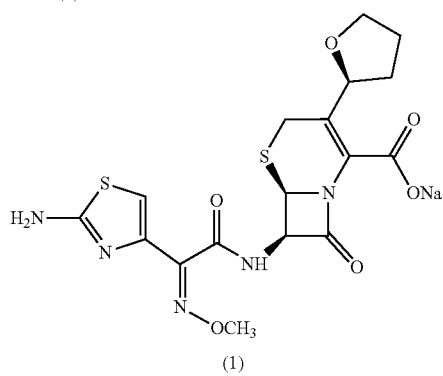

(1)

Introduction of the optically active tetrahydrofuran into the cephalosporin scaffold is complicated by the fact that (S)-2-(α-bromoacetyl)-THF (4b) must be prepared in-situ by reacting (S)-2-acetyl-tetrahydrofuran (4a) with molecular bromine, and subsequently reacted promptly with intermediate (3) because it is highly unstable. As a result, precautions have to be taken in the handling of this material. Moreover, the use of molecular bromine to generate (4b) is undesirable from an environmental, health and safety perspective.

Optically active (S)-2-acetyl-tetrahydrofuran (4a) can be prepared from (S)-2-carboxylic acid-THF (4) in a number of steps, or procured directly from a commercial source at a significant price premium. Either way, current methods for the preparation of bromo-compound (4b) leave the skilled person little choice but to use molecular halogens/molecular bromine.

Notwithstanding the state of the art there remains a need for improved methods for the synthesis of Cefovecin, in particular there remains a need for safer, cheaper routes to (S)-2-(α-bromoacetyl)-THF (4b), and related halogen equivalents.

Definitions

As used herein, the term C3-substituted cephalosporin refers to a cephalosporin in which the C3-position of the cephem ring structure is substituted, as illustrated in the below chemical structure.

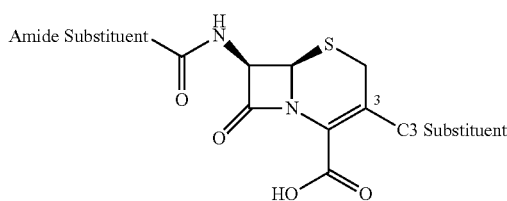

As used herein, the term $C_x$-$C_y$ aliphatic refers to linear, branched, saturated and unsaturated hydrocarbon chains comprising $C_x$-$C_y$ carbon atoms (and includes $C_x$-$C_y$ alkyl, $C_x$-$C_y$ alkenyl and $C_x$-$C_y$ alkynyl). Similarly, references to $C_x$-$C_y$ alkyl, $C_x$-$C_y$ alkenyl and $C_x$-$C_y$ alkynyl include linear and branched $C_x$-$C_y$ alkyl, $C_x$-$C_y$ alkenyl and $C_x$-$C_y$ alkynyl. The aliphatic chain may be substituted one or more times with a moiety selected from the group consisting of CN, $NO_2$, OH, $C_1$-$C_5$ alkoxy, $C_1$-$C_{10}$ ester, $C_1$-$C_{10}$ ketone, $C_1$-$C_{10}$ ketimine, $C_1$-$C_{10}$ sulfone, $C_1$-$C_{10}$ sulfoxide, a $C_1$-$C_{10}$ primary amide, and a $C_1$-$C_{20}$ secondary amide.

As used herein, the term "$C_x$-$C_y$ cycloaliphatic" refers to unfused, fused, spirocyclic, polycyclic, saturated and unsaturated hydrocarbon rings comprising $C_x$-$C_y$ carbon atoms (and includes $C_x$-$C_y$ cycloalkyl, $C_x$-$C_y$ cycloalkenyl and $C_x$-$C_y$ cycloalkynyl). The cycloaliphatic ring may be substituted one or more times with a moiety selected from the group consisting of CN, $NO_2$, OH, $C_1$-$C_5$ alkoxy, $C_1$-$C_{10}$ ester, $C_1$-$C_{10}$ ketone, $C_1$-$C_{10}$ ketimine, $C_1$-$C_{10}$ sulfone, $C_1$-$C_{10}$ sulfoxide, a $C_1$-$C_{10}$ primary amide, and a $C_1$-$C_{20}$ secondary amide.

The terms heteroaliphatic and heterocycloaliphatic embrace compounds of the above definitions, but where one or more carbon atoms of the hydrocarbon chains or hydrocarbon rings are replaced with at least one of O, N, P or S.

Cyclic compounds referred to in the present specification may be monocyclic or polycyclic, part of a fused ring system, or unfused.

As used herein, the terms aryl and aromatic are used interchangeably and refer to an aromatic carbocyclic structure which is monocyclic or polycyclic, part of a fused ring system, or unfused. Atoms of the aryl ring may be optionally substituted one or more times with a moiety selected from the group consisting of CN, $NO_2$, halogen, OH, $C_1$-$C_5$ alkoxy, $C_1$-$C_{10}$ ester, $C_1$-$C_{10}$ ketone, $C_1$-$C_{10}$ ketimine, $C_1$-$C_{10}$ sulfone, $C_1$-$C_{10}$ sulfoxide, a $C_1$-$C_{10}$ primary amide, and a $C_1$-$C_{20}$ secondary amide.

As used herein, the term heteroaromatic and heteroaryl are used interchangeably and refer to an aromatic heterocyclic structure having as ring members atoms of at least two different elements. The heterocycle may be monocyclic or polycyclic, part of a fused ring system, or unfused. Atoms of the heteroaryl ring may be optionally substituted one or more times with a moiety selected from the group consisting of CN, $NO_2$, halogen, OH, $C_1$-$C_5$ alkoxy, $C_1$-$C_{10}$ ester, $C_1$-$C_{10}$ ketone, $C_1$-$C_{10}$ ketimine, $C_1$-$C_{10}$ sulfone, $C_1$-$C_{10}$ sulfoxide, a $C_1$-$C_{10}$ primary amide, and a $C_1$-$C_{20}$ secondary amide.

SUMMARY OF THE INVENTION

The present invention provides for safer more efficient routes to C3-substituted cephalosporins. Whilst the methodology is generally applicable to a variety of C3-substituted cephalosporins, it finds particular use in the synthesis of Cefovecin.

Accordingly, in a first aspect the present invention provides for a method of synthesising a C3-substituted cephalosporin comprising the steps of:

(i) generating a compound of the formula (II) from a compound of the formula (I)

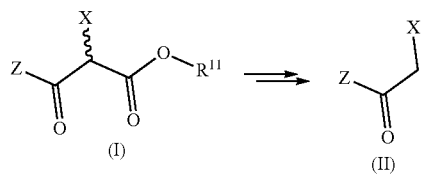

(ii) reacting the compound of formula (II) with a thiol of the formula (III-1) or (III-2) to yield a compound of the formula (IV-1) or (IV-2), and

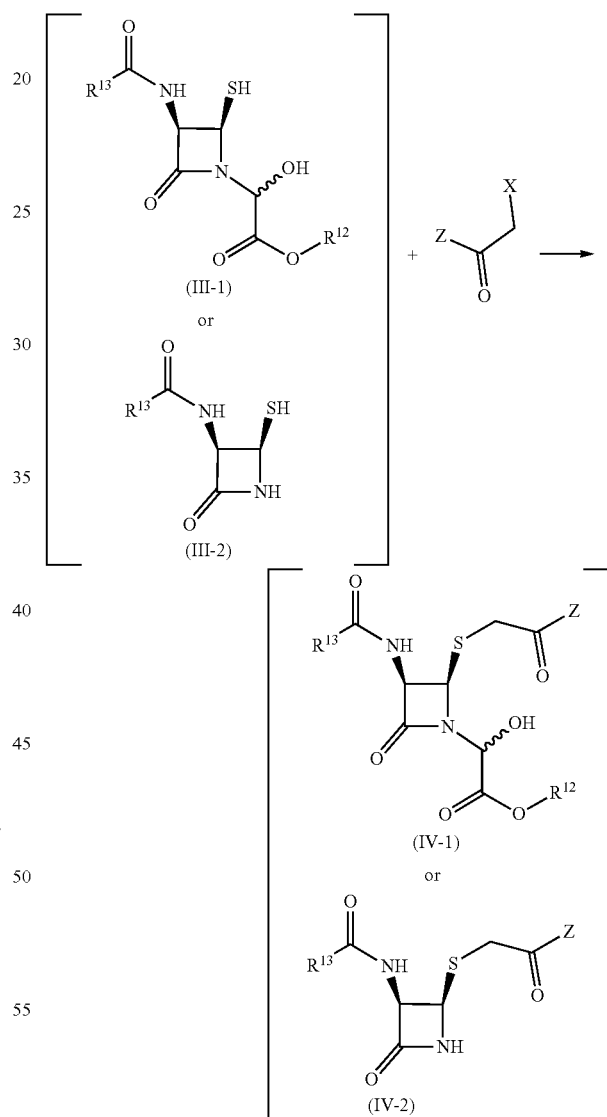

(iii) further processing the compound of formula (IV-1) or (IV-2) to yield a C3-substituted cephalosporin, wherein
Z is selected from the group consisting of $C_1$-$C_{20}$ aliphatic, $C_3$-$C_{20}$ cycloaliphatic, $C_2$-$C_{20}$ heteroaliphatic, $C_2$-$C_{20}$ heterocycloaliphatic, $C_6$-$C_{20}$ aryl, $C_2$-$C_{20}$ heteroaryl, and combinations thereof;

X is selected from the group consisting of Cl, Br, and I; and $R^{11}$, $R^{12}$, $R^{13}$ are the same or different and are independently selected from the group consisting of H, $C_1$-$C_{20}$ aliphatic, $C_3$-$C_{20}$ cycloaliphatic, $C_2$-$C_{20}$ heteroaliphatic, $C_2$-$C_{20}$ heterocycloaliphatic, $C_6$-$C_{20}$ aryl, $C_2$-$C_{20}$ heteroaryl, and combinations thereof.

In one embodiment, Z is selected from the group consisting of $C_3$-$C_{20}$ cycloaliphatic, $C_2$-$C_{20}$ heterocycloaliphatic, $C_6$-$C_{20}$ aryl, $C_2$-$C_{20}$ heteroaryl, and combinations thereof. For example, Z may be selected from the group consisting of $C_2$-$C_{20}$ heterocycloaliphatic, and $C_2$-$C_{20}$ heteroaryl. Preferably, Z is selected from the group consisting of tetrahydrofuranyl, tetrahydrothiophenyl, and tetrahydropyrrolyl. In a particularly preferred embodiment Z is 2-tetrahydrofuranyl, for example where Z is 2-tetrahydrofuranyl and $C_2$ on the tetrahydrofuran ring has the (S) stereochemical configuration.

In one embodiment, X is Br or Cl.

In one embodiment $R^{11}$ is $C_1$-$C_{20}$ aliphatic. For example, $R^{11}$ may be $C_1$-$C_{20}$ alkyl. In a preferred embodiment $R^{11}$ is tertiary-butyl.

In one embodiment, $R^{12}$ is selected from the group consisting of $C_1$-$C_{20}$ aliphatic, $C_6$-$C_{20}$ aryl, $C_2$-$C_{20}$ heteroaryl, and combinations thereof. For example, $R^{12}$ may be selected from the group consisting $C_1$-$C_{20}$ aliphatic, $C_6$-$C_{20}$ aryl, and combinations thereof. In a preferred embodiment, $R^{12}$ is para-nitrobenzyl.

In one embodiment, $R^{13}$ is selected from the group consisting of $C_1$-$C_{20}$ aliphatic, $C_6$-$C_{20}$ aryl, $C_2$-$C_{20}$ heteroaryl, and combinations thereof. For example, $R^{13}$ may be selected from the group consisting $C_1$-$C_{20}$ aliphatic, $C_6$-$C_{20}$ aryl, and combinations thereof. In a preferred embodiment, $R^{13}$ is benzyl.

In one embodiment, Z is selected from the group consisting of $C_2$-$C_{20}$ heterocycloaliphatic, and $C_2$-$C_{20}$ heteroaryl, and $R^{11}$ is $C_1$-$C_{20}$ aliphatic. For example, Z may be selected from the group consisting of $C_2$-$C_{20}$ heterocycloaliphatic, and $C_2$-$C_{20}$ heteroaryl and $R^{11}$ may be $C_1$-$C_{20}$ alkyl. In a preferred embodiment Z is selected from the group consisting of tetrahydrofuranyl, tetrahydrothiophenyl, and tetrahydropyrrolyl and $R^{11}$ is tertiary-butyl. For example, Z may be 2-tetrahydrofuranyl (and C2 on the tetrahydrofuran ring has the (S) stereochemical configuration) and $R^{11}$ may be tertiary-butyl.

In one embodiment, Z is selected from the group consisting of $C_2$-$C_{20}$ heterocycloaliphatic, and $C_2$-$C_{20}$ heteroaryl, $R^{11}$ is $C_1$-$C_{20}$ aliphatic, and $R^{12}$ is selected from the group consisting $C_1$-$C_{20}$ aliphatic, $C_6$-$C_{20}$ aryl, and combinations thereof. For example, Z may be selected from the group consisting of $C_2$-$C_{20}$ heterocycloaliphatic, and $C_2$-$C_{20}$ heteroaryl, $R^{11}$ may be $C_1$-$C_{20}$ alkyl, and $R^{12}$ may be selected from the group consisting $C_1$-$C_{20}$ aliphatic, $C_6$-$C_{20}$ aryl, and combinations thereof. In a preferred embodiment Z is selected from the group consisting of tetrahydrofuranyl, tetrahydrothiophenyl, and tetrahydropyrrolyl, $R^{11}$ is tertiary-butyl, and $R^{12}$ is para-nitrobenzyl. For example, Z may be 2-tetrahydrofuranyl (and optionally C2 on the tetrahydrofuran ring has the (S) stereochemical configuration), $R^{11}$ may be tertiary-butyl, and $R^{12}$ may be para-nitrobenzyl.

In one embodiment, Z is selected from the group consisting of $C_2$-$C_{20}$ heterocycloaliphatic, and $C_2$-$C_{20}$ heteroaryl, $R^{11}$ is $C_1$-$C_{20}$ aliphatic, $R^{12}$ is selected from the group consisting $C_1$-$C_{20}$ aliphatic, $C_6$-$C_{20}$ aryl, and combinations thereof, and $R^{13}$ is selected from the group consisting of $C_1$-$C_{20}$ aliphatic, $C_6$-$C_{20}$ aryl, $C_2$-$C_{20}$ heteroaryl, and combinations thereof. For example, Z may be selected from the group consisting of $C_2$-$C_{20}$ heterocycloaliphatic, and $C_2$-$C_{20}$ heteroaryl, $R^{11}$ may be $C_1$-$C_{20}$ alkyl, $R^{12}$ may be selected from the group consisting $C_1$-$C_{20}$ aliphatic, $C_6$-$C_{20}$ aryl, and combinations thereof, and $R^{13}$ may be selected from the group consisting $C_1$-$C_{20}$ aliphatic, $C_6$-$C_{20}$ aryl, and combinations thereof. In a preferred embodiment Z is selected from the group consisting of tetrahydrofuranyl, tetrahydrothiophenyl, and tetrahydropyrrolyl, $R^{11}$ is tertiary-butyl, $R^{12}$ is para-nitrobenzyl, and $R^{13}$ is benzyl. For example, Z may be 2-tetrahydrofuranyl (and optionally $C_2$ on the tetrahydrofuran ring has the (S) stereochemical configuration), $R^{11}$ may be tertiary-butyl, $R^{12}$ may be para-nitrobenzyl, and $R^{13}$ may be benzyl.

In one embodiment, Z is selected from the group consisting of $C_2$-$C_{20}$ heterocycloaliphatic, and $C_2$-$C_{20}$ heteroaryl, X is Br or Cl, and $R^{11}$ is $C_1$-$C_{20}$ aliphatic. For example, Z may be selected from the group consisting of $C_2$-$C_{20}$ heterocycloaliphatic, and $C_2$-$C_{20}$ heteroaryl, X may be Br or Cl, and $R^{11}$ may be $C_1$-$C_{20}$ alkyl. In a preferred embodiment Z is selected from the group consisting of tetrahydrofuranyl, tetrahydrothiophenyl, and tetrahydropyrrolyl, X is Br or Cl, and $R^{11}$ is tertiary-butyl. For example, Z may be 2-tetrahydrofuranyl (and optionally $C_2$ on the tetrahydrofuran ring has the (S) stereochemical configuration), X may be Br or Cl, and $R^{11}$ may be tertiary-butyl.

In one embodiment, Z is selected from the group consisting of $C_2$-$C_{20}$ heterocycloaliphatic, and $C_2$-$C_{20}$ heteroaryl, $R^{11}$ is $C_1$-$C_{20}$ aliphatic, X is Br or Cl, and $R^{12}$ is selected from the group consisting $C_1$-$C_{20}$ aliphatic, $C_6$-$C_{20}$ aryl, and combinations thereof. For example, Z may be selected from the group consisting of $C_2$-$C_{20}$ heterocycloaliphatic, and $C_2$-$C_{20}$ heteroaryl, $R^{11}$ may be $C_1$-$C_{20}$ alkyl, X may be Br or Cl, and $R^{12}$ may be selected from the group consisting $C_1$-$C_{20}$ aliphatic, $C_6$-$C_{20}$ aryl, and combinations thereof. In a preferred embodiment Z is selected from the group consisting of tetrahydrofuranyl, tetrahydrothiophenyl, and tetrahydropyrrolyl, $R^{11}$ is tertiary-butyl, X is Br or Cl, and $R^{12}$ is para-nitrobenzyl. For example, Z may be 2-tetrahydrofuranyl (and optionally $C_2$ on the tetrahydrofuran ring has the (S) stereochemical configuration), $R^{11}$ may be tertiary-butyl, X may be Br or Cl, and $R^{12}$ may be para-nitrobenzyl.

In one embodiment, Z is selected from the group consisting of $C_2$-$C_{20}$ heterocycloaliphatic, and $C_2$-$C_{20}$ heteroaryl, X is Br or Cl, $R^{11}$ is $C_1$-$C_{20}$ aliphatic, $R^{12}$ is selected from the group consisting $C_1$-$C_{20}$ aliphatic, $C_6$-$C_{20}$ aryl, and combinations thereof, and $R^{13}$ is selected from the group consisting of $C_1$-$C_{20}$ aliphatic, $C_6$-$C_{20}$ aryl, $C_2$-$C_{20}$ heteroaryl, and combinations thereof. For example, Z may be selected from the group consisting of $C_2$-$C_{20}$ heterocycloaliphatic, and $C_2$-$C_{20}$ heteroaryl, X may be Br or Cl, $R^{11}$ may be $C_1$-$C_{20}$ alkyl, $R^{12}$ may be selected from the group consisting $C_1$-$C_{20}$ aliphatic, $C_6$-$C_{20}$ aryl, and combinations thereof, and $R^{13}$ may be selected from the group consisting $C_1$-$C_{20}$ aliphatic, $C_6$-$C_{20}$ aryl, and combinations thereof. In a preferred embodiment Z is selected from the group consisting of tetrahydrofuranyl, tetrahydrothiophenyl, and tetrahydropyrrolyl, X is Br or Cl, $R^{11}$ is tertiary-butyl, $R^{12}$ is para-nitrobenzyl, and $R^{13}$ is benzyl. For example, Z may be 2-tetrahydrofuranyl (and optionally C2 on the tetrahydrofuran ring has the (S) stereochemical configuration), X may be Br or Cl, $R^{11}$ may be tertiary-butyl, $R^{12}$ may be para-nitrobenzyl, and $R^{13}$ may be benzyl.

The step of generating a compound of the formula (II) from a compound of the formula (I), namely:

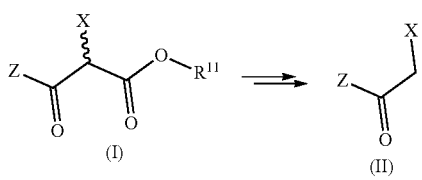

may comprise hydrolysis of $C(O)OR^{11}$ to the corresponding carboxylic acid, and decarboxylating the resulting beta-keto acid. Advantageously, compounds of the general formula (I) are storage stable when isolated and when kept in solution. This has significant advantages from a handling perspective. Compounds of the general formula (II) are too reactive to be stored for any appreciable length of time.

Further advantageously, compounds of the general formula (I) yield reactive halogen intermediates of the general formula (II) without the need to include harmful molecular halogens, e.g. $Br_2$, $Cl_2$, $I_2$ in the synthetic process. As previously discussed, and illustrated in the below scheme for ease of reference, prior art methods of generating reactive intermediates of the general formula (II) [illustrated below for one particular embodiment, namely compound 4b] require bromination of intermediate 4a with molecular bromine to generate reactive intermediate 4b. Naturally, the use of and handling of molecular halogens such as $Br_2$ is not desirable from an environmental, health and safety perspective.

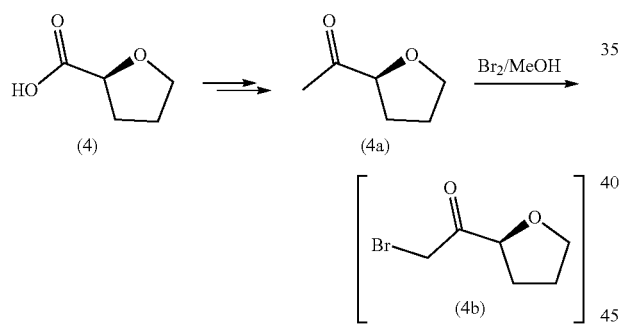

Compounds of the general formula (I) can be prepared as outlined immediately below. Without prejudice to the generality of the method of the present invention, the preparation of compounds of the general formula (I) is illustrated for the particular embodiment of a furan derivative (starting from carboxylic acid 4) for the sake of clarity. However, the skilled person will appreciate that the methodology is generally applicable for compounds within the definitions encompassed by the previously defined variables X, Z, $R^{11}$, $R^{12}$ and $R^{13}$.

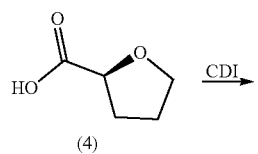

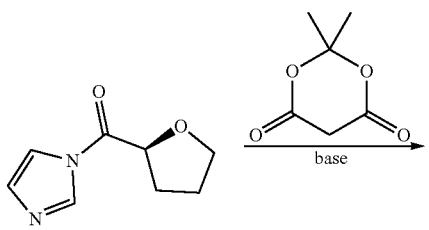

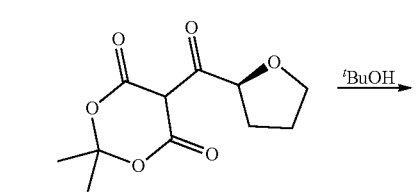

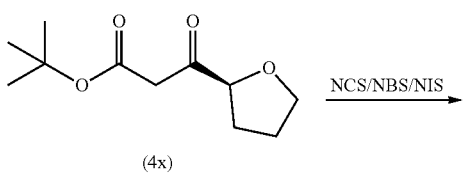

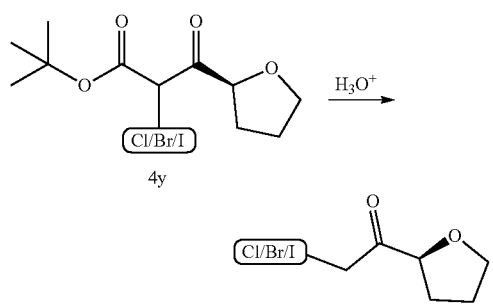

Carboxylic acid 4 is activated by reacting it with carbonyldiimidazole (CDI). The resulting activated acid is reacted with Meldrum's acid in base, and hydrolysis with tert-butanol yields beta-keto ester 4x. 4x is capable of reacting with mild halogenation agents such as N-bromosuccinimide (NBS), N-chlorosuccinimide (NCS), or N-iodosuccinimide (NIS) to yield halogenated compounds 4y [which are of the general formula (I)]. Halogenated beta-keto ester (4y) can be hydrolysed to the corresponding carboxylic acid and decarboxylated to yield the reactive halogen compounds.

This is highly advantageous from a handling, environmental, health and safety perspective. The present inventors found that intermediate 4a utilised in the prior art (see [0033]) could not be halogenated with milder halogenating reagents. Thus, the present inventors have devised a safer, more user friendly route to compounds of the general formula (II).

The step of further processing the compound of formula (IV-1) or (IV-2) to yield a C3-substituted cephalosporin (see immediately below) entails standard synthetic transformations employed in the synthesis of C3-substituted cephalosporins.

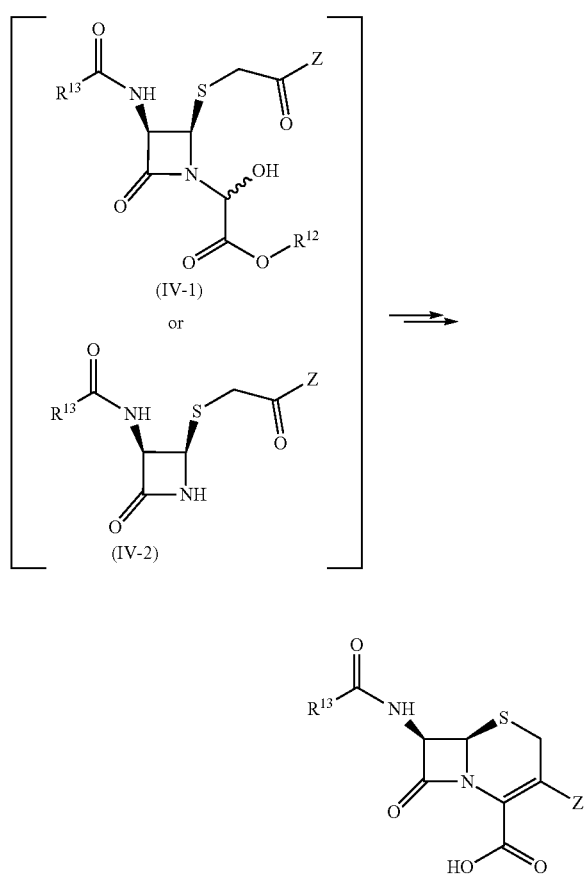

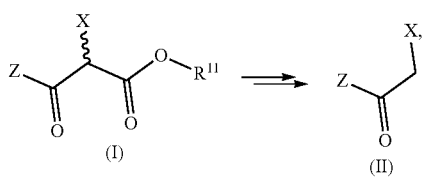

and further wherein
Z is selected from the group consisting of $C_1$-$C_{20}$ aliphatic, $C_3$-$C_{20}$ cycloaliphatic, $C_2$-$C_{20}$ heteroaliphatic, $C_2$-$C_{20}$ heterocycloaliphatic, $C_6$-$C_{20}$ aryl, $C_2$-$C_{20}$ heteroaryl, and combinations thereof;
X is selected from the group consisting of Cl, Br, and I; and
$R^{11}$ is selected from the group consisting of H, $C_1$-$C_{20}$ aliphatic, $C_3$-$C_{20}$ cycloaliphatic, $C_2$-$C_{20}$ heteroaliphatic, $C_2$-$C_{20}$ heterocycloaliphatic, $C_6$-$C_{20}$ aryl, $C_2$-$C_{20}$ heteroaryl, and combinations thereof.

In one embodiment, Z is selected from the group consisting of $C_3$-$C_{20}$ cycloaliphatic, $C_2$-$C_{20}$ heterocycloaliphatic, $C_6$-$C_{20}$ aryl, and $C_2$-$C_{20}$ heteroaryl. For example, Z may be selected from the group consisting of $C_2$-$C_{20}$ heterocycloaliphatic, and $C_2$-$C_{20}$ heteroaryl. Preferably, Z is selected from the group consisting of tetrahydrofuranyl, tetrahydrothiophenyl, and tetrahydropyrrolyl. In a particularly preferred embodiment Z is 2-tetrahydrofuranyl, for example where Z is 2-tetrahydrofuranyl and optionally C2 on the tetrahydrofuran ring has the (S) stereochemical configuration.

In one embodiment $R^{11}$ is $C_1$-$C_{20}$ aliphatic. For example, $R^{11}$ may be $C_1$-$C_{20}$ alkyl. In a preferred embodiment $R^{11}$ is tertiary-butyl.

In one embodiment X is Br or Cl.

In one embodiment, Z is selected from the group consisting of $C_2$-$C_{20}$ heterocycloaliphatic, and $C_2$-$C_{20}$ heteroaryl, and $R^{11}$ is $C_1$-$C_{20}$ aliphatic. For example, Z may be selected from the group consisting of $C_2$-$C_{20}$ heterocycloaliphatic, and $C_2$-$C_{20}$ heteroaryl and $R^{11}$ may be $C_1$-$C_{20}$ alkyl. In a preferred embodiment Z is selected from the group consisting of tetrahydrofuranyl, tetrahydrothiophenyl, and tetrahydropyrrolyl and $R^{11}$ is tertiary-butyl. For example, Z may be 2-tetrahydrofuranyl (and optionally C2 on the tetrahydrofuran ring has the (S) stereochemical configuration) and $R^{11}$ may be tertiary-butyl.

In one embodiment, Z is selected from the group consisting of $C_2$-$C_{20}$ heterocycloaliphatic, and $C_2$-$C_{20}$ heteroaryl, X is Br or Cl, and $R^{11}$ is $C_1$-$C_{20}$ aliphatic. For example, Z may be selected from the group consisting of $C_2$-$C_{20}$ heterocycloaliphatic, and $C_2$-$C_{20}$ heteroaryl, X may be Br or Cl, and $R^{11}$ may be $C_1$-$C_{20}$ alkyl. In a preferred embodiment Z is selected from the group consisting of tetrahydrofuranyl, tetrahydrothiophenyl, and tetrahydropyrrolyl, X is Br or Cl, and $R^{11}$ is tertiary-butyl. For example, Z may be 2-tetrahydrofuranyl (and optionally C2 on the tetrahydrofuran ring has the (S) stereochemical configuration), X may be Br or Cl, and $R^{11}$ may be tertiary-butyl.

In yet a further aspect, the present invention provides for a compound of the formula (V), wherein:

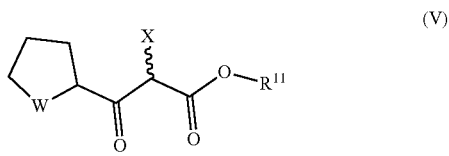

For example, in the case of intermediate (IV-1) the hydroxyl group alpha to the ester $C(O)OR^{12}$ can be converted to a halogen, which in turn can be converted into a phosphorus ylid. The phosphorous ylid readily cyclises using Wittig chemistry to yield a C3-substituted cephalosporin. The —$NHC(O)R^{13}$ amide identity can be tailored to the particular C3-substituted cephalosporin required. In the case of Cefovecin, the standard further processing steps can be found in *Process Chemistry in the Pharmaceutical Industry, Volume* 2: Challenges in an ever changing climate, Edited by K Gadamasetti & T Braish, CRC press 2008, Chapter 11, pg 191-204 (Timothy Norris), the disclosure of which is incorporated herein by reference.

Similarly, in the case of intermediate (IV-2) the beta-lactam nitrogen can be alkylated with an ester of glyoxylic acid to yield a compound similar to intermediate (IV-1), which is further processed as per the previous paragraph. Further particulars can be found in J. H. Bateson et al., *The Journal of Antibiotics*, Vol 47 (2), 1994, 253-256, the disclosure of which is incorporated herein by reference.

Alternatively, standard further processing of intermediates (IV-1) and (IV-2) is also disclosed in patent publications WO9201695, WO9201696, GB2300856, EP1178049, WO0246199, WO0246198, and WO05092900. The disclosures of all of which are incorporated herein by reference.

In another aspect, the present invention provides for use of a compound of the general formula (I) in the synthesis of a C3-substituted cephalosporin, wherein the compound of formula (I) is processed to yield a reactive intermediate of formula (II):

W is selected from the group consisting of O, S, and N, more preferably W is selected from the group consisting of O, S, and NH;

X is selected from the group consisting of Cl, Br, and I; and $R^{11}$ is selected from the group consisting of H, $C_1$-$C_{20}$ aliphatic, $C_3$-$C_{20}$ cycloaliphatic, $C_2$-$C_{20}$ heteroaliphatic, $C_2$-$C_{20}$ heterocycloaliphatic, $C_6$-$C_{20}$ aryl, $C_2$-$C_{20}$ heteroaryl, and combinations thereof.

In one embodiment, $R^{11}$ is $C_1$-$C_{20}$ aliphatic. For example, $R^{11}$ may be $C_1$-$C_{20}$ alkyl. In a preferred embodiment $R^{11}$ is tertiary-butyl.

In one embodiment, W is O or N, preferably W is O or NH. For example, W may be O.

In one embodiment, X is Br or Cl.

In one embodiment, $R^{11}$ is $C_1$-$C_{20}$ aliphatic, and W is O or N, preferably W is O or NH. For example, $R^{11}$ may be $C_1$-$C_{20}$ alkyl, and W may be O or N, preferably W is O or NH. In a particularly preferred embodiment, $R^{11}$ is tertiary-butyl and W is O.

In one embodiment, $R^{11}$ is $C_1$-$C_{20}$ aliphatic, X is Br, and W is O or N, preferably W is O or NH. For example, $R^{11}$ may be $C_1$-$C_{20}$ alkyl, X may be Br or Cl, and W may be O or N, preferably W is O or NH. In a particularly preferred embodiment, $R^{11}$ is tertiary-butyl, X is Br or Cl, and W is O.

In general, in the compound of formula (V), it is preferable that $R^{11}$ is not ethyl when W=O and X=$C_1$. More preferably, $R^{11}$ is $C_1$ aliphatic or $C_3$-$C_{20}$ aliphatic, particularly $C_1$ alkyl or $C_3$-$C_{20}$ alkyl, when W=O and X=Cl.

Where suitable, it will be appreciated that all optional and/or preferred features of one embodiment of the invention may be combined with optional and/or preferred features of another/other embodiment(s) of the invention.

DETAILED DESCRIPTION OF THE INVENTION

It should be readily apparent to one of ordinary skill in the art that the examples disclosed herein below represent generalised examples only, and that other arrangements and methods capable of reproducing the invention are possible and are embraced by the present invention.

Cefovecin is a preferred C3-Substituted Cephalosporin within the scope of the aspects of the present invention. An outline of the synthesis of Cefovecin from start to finish is illustrated in B the scheme below. Further particulars of the synthesis can be found in the citations disclosed supra.

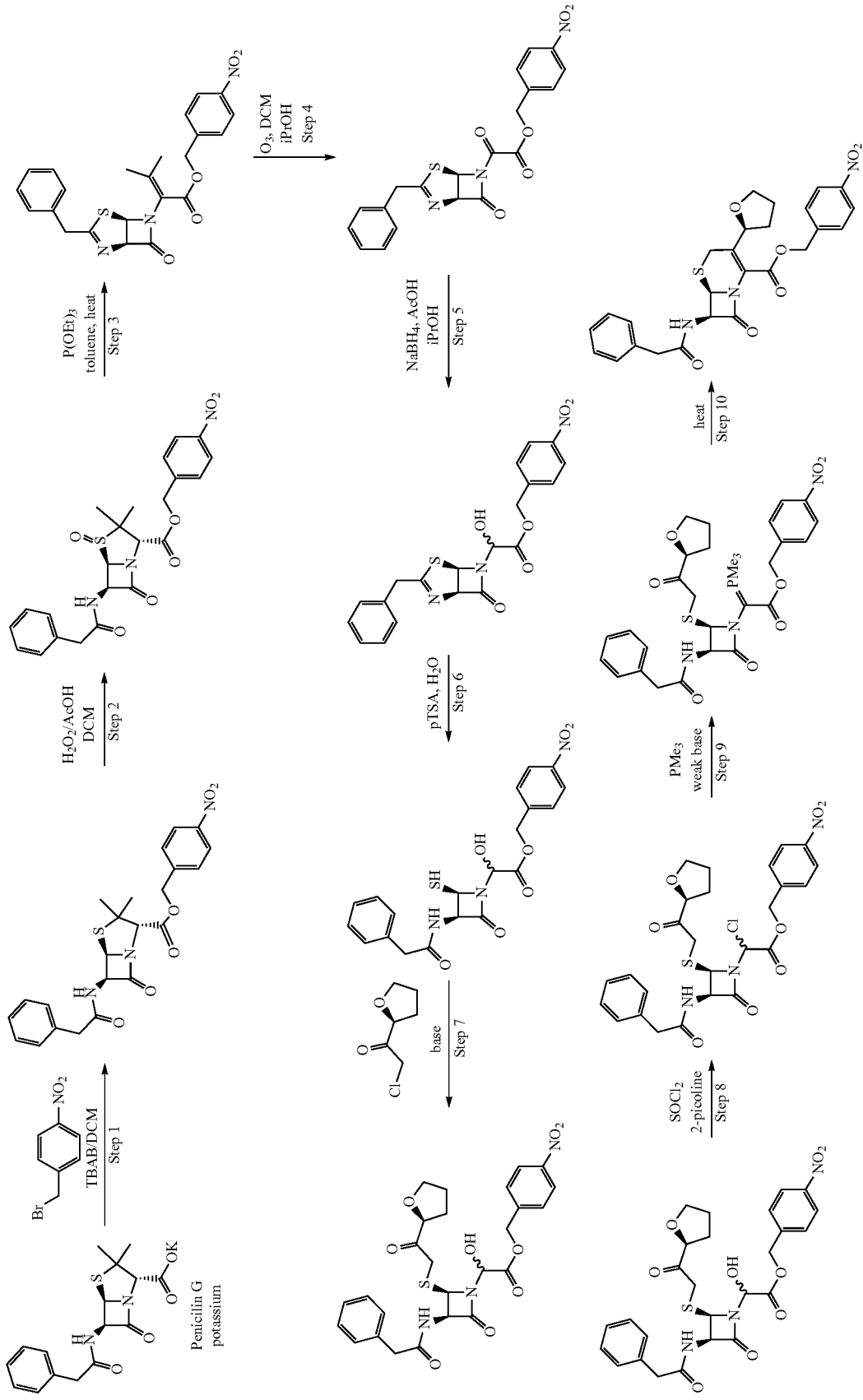

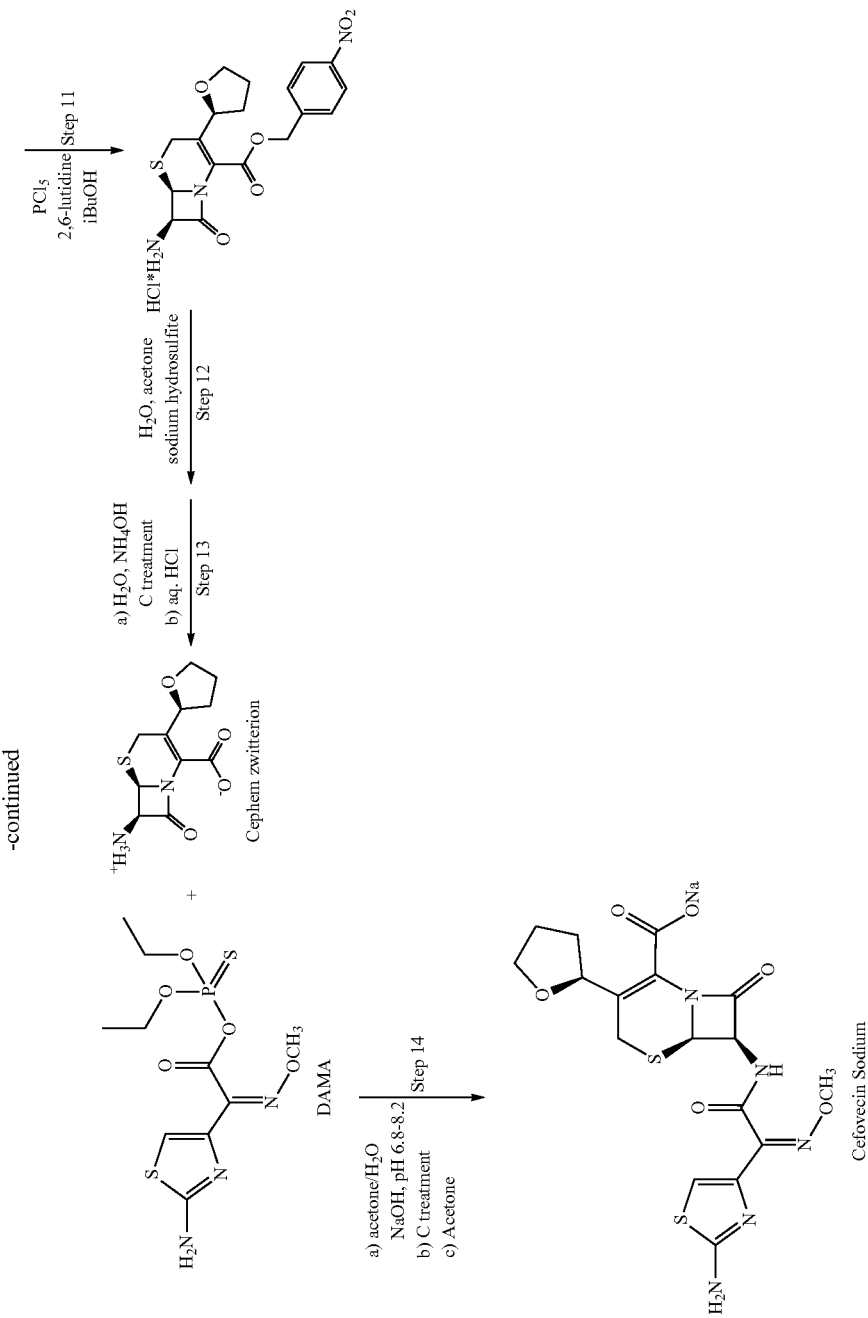

In the schematic above, an embodiment of the present invention is best illustrated by step 7; in particular the preparation of the reactive chlorofuran intermediate. Detailed methods for the preparation of this compound, and its coupling to the thiol as illustrated in step 7 are outlined here under.

Stage (i): Formation of 1,3-Dioxane-4,6-dione-2,2-dimethyl-5-[[(2S)-tetrahydro-2-furanyl]carbonyl]

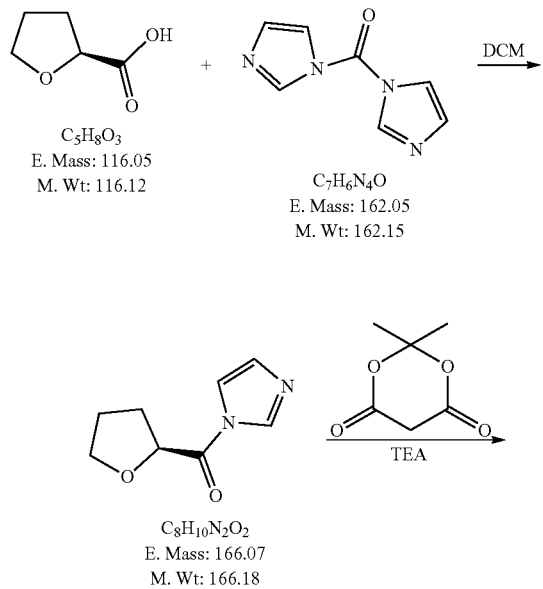

(S)-THF acid (20 g, 0.17 moles) was dissolved in dichloromethane (100 mL, 1.7 M) and the resulting solution was stirred at room temperature. Carbonyldiimidazole (30.7 g, 1.1 eq.) was added portion-wise to this solution at room temperature and stirred for 3 hours. The reaction mixture was cooled to 0-5° C., then charged with Meldrum's acid (2.23 g, 0.9 eq.) and triethylamine (4.8 mL, 0.2 eq.) maintaining the temperature at 0-5° C. The reaction mixture was stirred at this temperature for 1-3 h. The resulting solution was warmed to room temperature and WFI (100 mL) was added. The organic layer was separated, charged with a 36% solution of HCl (100 mL) and then stirred at room temperature for 1-3 h, until a precipitate was obtained. The solid is filtered and washed with WFI (3×50 mL). Isolated yield 25.4 g, 61%. [M+1] 243.16. 1Hδ (DMSO-D6, 400 MHz): 1.73 (s, 6H), 1.94-1.96 (m, 1H), 2.00-2.02 (m, 2H), 2.55-2.57 (m, 1H), 4.08-4.10 (m, 2H), 4.11-4.14 (m, 2H), 5.64 (t, 1H, J=2.8).

Stage (ii): Formation of 3-Oxo-3-[2(S)-tetrahydrofuranyl] propionic acid tert-butyl ester

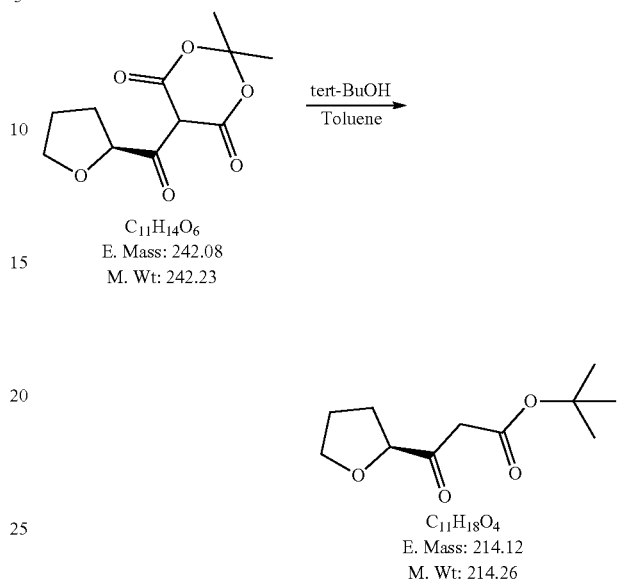

1,3-Dioxane-4,6-dione-2,2-dimethyl-5-[[(2S)-tetrahydro-2-furanyl]carbonyl] (25.4 g, 0.1 moles) was dissolved in toluene (150 mL, 0.7 M) at room temperature. To the resulting solution tert-BuOH (49.4 mL, 5 eq.) was charged, the reaction mixture is then warmed to 80-85° C. and stirred for 3-4 h. The reaction mass was cooled down to 10-15° C. and saturated NaHCO₃ solution (100 mL) was added gradually until a pH of ~8.0-8.5 was obtained. The organic layer was separated and the aqueous layer further extracted with toluene (2×50 mL). The organic layers were combined and washed with WFI (2×100 mL). The layers were separated and the organic layer was concentrated under vacuum at less than 50° C. until approx. 50 mL (2 V, 2.3 M) remained. A solvent exchange was then undertaken whereby dichloromethane was added (3×80 mL) and upon final addition the solvent volume was concentrated to ~50 mL (2 V, 2.3 M). The resulting solution was carried directly on to the next step. Yield: 21 g, 93%. [M+1]=215.18. 1Hδ (DMSO-d6, 400 MHz): 1.43 (s 9H), 1.53-1.56 (m, 1H), 1.89-1.92 (m, 2H), 1.94-1.96 (m, 1H), 3.45 (t, 2H, J=3.2 Hz), 3.86-3.89 (m, 2H), 4.32-4.35 (m, 1H).

Stage (iii): Formation of 3-Oxo-3-[2(S)-tetrahydrofuranyl]-2-Chloro propionic acid tert-butyl ester

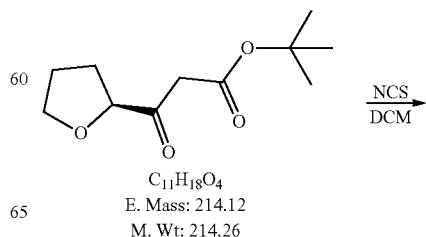

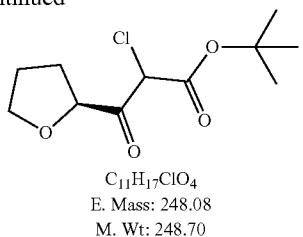

C₁₁H₁₇ClO₄
E. Mass: 248.08
M. Wt: 248.70

3-Oxo-3-[2(S)-tetrahydrofuranyl] propionic acid tert-butyl ester (21 g, 0.98 moles) in dichloromethane (40 mL, 2.3 M) was diluted further with dichloromethane (63 mL) at room temperature. The mixture was cooled to 0-5° C. and N-chlorosuccinimide (1.25 eq.) was added drop-wise over a 15 min period. The reaction mixture was heated to room temperature and stirred for 1-3 h. The solution was then cooled down to 5-10° C., after which the slow addition of sat. NaHCO₃ solution occurred until a pH ~8.0-8.5 was obtained. This addition must be carried out whilst maintaining the temperature below 25° C. The organic layer was separated and the aqueous layer was further extracted with dichloromethane (2×100 mL). The organic layers were combined, washed with WFI (2×250 mL) and reduced under vacuum maintaining the temperature at less than 50° C. The layers were concentrated until a volume of ~40 mL (2V, 0.14 M) and the resulting solution was used directly in the next step. Yield: 18 g, 74%. [M+1]=249.12. 1Hδ (DMSO-d6, 400 MHz): 1.45 (s, 9H), 1.86-1.87 (m, 2H), 2.01-2.04 (m, 1H), 2.23-2.26 (m, 1H), 3.82-2.85 (m, 2H), 4.54-4.57 (m, 1H), 5.06 (d, 1H, J=4.2 Hz).

Stage (iv): Formation of Ethanone-2-chloro-1-[(2S)-tetrahydro-2-furanyl]

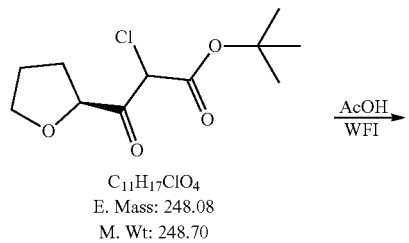

C₁₁H₁₇ClO₄
E. Mass: 248.08
M. Wt: 248.70

AcOH / WFI

C₆H₉ClO₂
E. Mass: 148.03
M. Wt: 148.59

3-Oxo-3-[2(S)-tetrahydrofuranyl]-2-Chloro propionic acid tert-butyl ester (18 g, 0.07 moles) in dichloromethane (0.14 M) was charged with acetic acid (35 mL, 8.4 eq) and WFI (35 mL) at room temperature. The reaction mixture was heated to 105-108° C. and stirred at same temperature for 4-5 h. After completion of reaction the resulting solution was cooled to 5-10° C. The slow addition of sat. NaHCO3 solution was undertaken until pH 8.0-8.5 is obtained, maintaining the temperature <25° C. Dichloromethane (300 mL) was charged followed by the separation of the organic layer. The aqueous layer was further extracted with dichloromethane (2×300 mL), all three organic layers were combined and washed with WFI (2×400 mL). The organic layer was concentrated under vacuum at a temperature less than 50° C. until approx. 40 mL (2V, 0.07 M) and used in directly in the next reaction (coupling reaction). Yield: 10.9 g, 42.7% overall. [M+1]=149.12. 1Hδ (DMSO-d6, 400 MHz): 1.91-1.93 (m, 2H), 1.95-1.98 (m, 1H), 2.23-2.24 (m, 1H), 3.91-3.93 (m, 2H), 4.42-4.45 (m, 2H), 4.43-4.46 (m, 1H).

Stage (v): Coupling

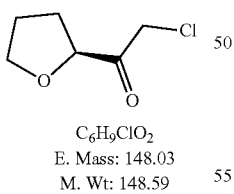

Thiol (4 g, 8.9 mmoles) was suspended in dichloromethane (16 mL, 0.2 M). Then, ethanone-2-chloro-1-[(2S)-tetrahydro-2-furanyl] (0.9 g, 1.1 eq. in 0.07 M dichloromethane) was charged at room temperature. To this reaction mixture dimethyl acetamide (3.2 mL, 1.2 M) was added and the reaction mass stirred at room temperature for 10-14 h. After which, WFI (15 mL) was charged, stirred for 15 mins and the layers are separated. The aqueous layer was extracted twice with dichloromethane (2×15 mL). The organic layers were combined and washed with WFI (2×20 mL) followed by sat. NaCl solution (20 mL). The organic layer was separated and concentrated under vacuum to ~20 mL (1V, 0.7 M). The resulting solution was added slowly to n-Hexane (80 mL) and the resulting precipitate was filtered and washed with n-hexane (2×10 mL) resulting in an off-white powder. Yield: 4.3 g, 86%. [M+1]=558.19. 1Hδ (CDCl3, 400 MHz): 1.81-1.84 (m, 2H), 2.08-2.11 (m, 2H), 2.02 (s, 1H), 2.99-3.02 (m, 1H), 2.48-3.52 (m, 2H), 3.61 (s, 1H), 3.84-3.88 (m, 2H), 4.32 (br. s, 1H, —OH), 5.04-5.08 (m, 1H), 5.31-5.36 (m, 3H, —CH2 and NH), 5.54 (d, 1H, J=4.2 Hz), 6.82-6.84 (m, 1H), 7.24-7.29 (m, 4H), 7.53-7.57 (m, 2H), 8.18-8.21 (m, 2H).

The words "comprises/comprising" and the words "having/including" when used herein with reference to the present invention are used to specify the presence of stated features, integers, steps or components but do not preclude the presence or addition of one or more other features, integers, steps, components or groups thereof.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

The invention claimed is:

1. A method of synthesising a C3-substituted cephalosporin comprising steps of:
   (i) generating a compound of the formula (II) from a compound of the formula (I)

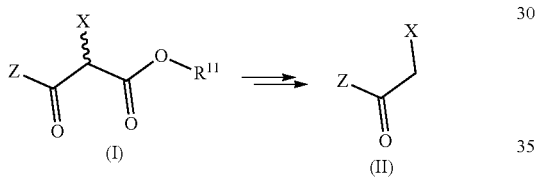

(ii) reacting the compound of formula (II) with a thiol of the formula (III-1) or (III-2) to yield a compound of the formula (IV-1) or (IV-2), and

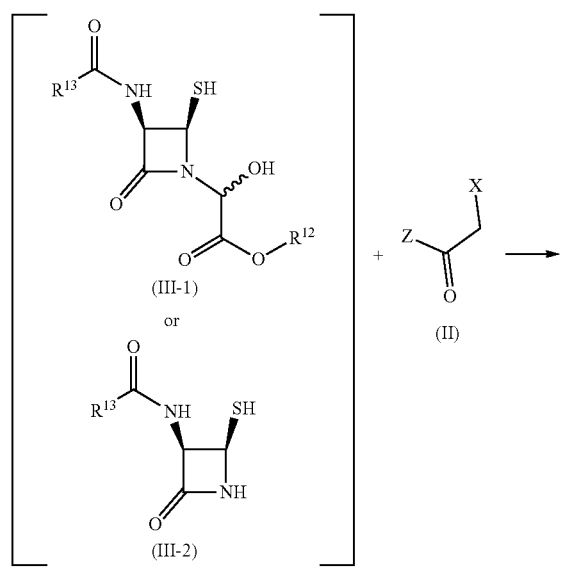

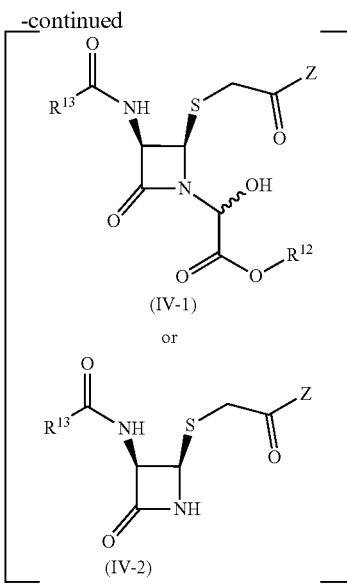

(iii) further processing the compound of formula (IV-1) or (IV-2) to yield a C3-substituted cephalosporin, wherein Z is selected from the group consisting of $C_1$-$C_{20}$ aliphatic, $C_3$-$C_{20}$ cycloaliphatic, $C_2$-$C_{20}$ heteroaliphatic, $C_2$-$C_{20}$ heterocycloaliphatic, $C_6$-$C_{20}$ aryl, $C_2$-$C_{20}$ heteroaryl, and combinations thereof;

X is selected from the group consisting of Cl, Br, and I; and $R^{11}$, $R^{12}$, $R^{13}$ are the same or different and each of $R^{11}$, $R^{12}$, $R^{13}$ is either H or is independently selected from the group consisting of $C_1$-$C_{20}$ aliphatic, $C_3$-$C_{20}$ cycloaliphatic, $C_2$-$C_{20}$ heteroaliphatic, $C_2$-$C_{20}$ heterocycloaliphatic, $C_6$-$C_{20}$ aryl, $C_2$-$C_{20}$ heteroaryl, and combinations thereof.

2. The method of claim 1 wherein Z is selected from the group consisting of $C_3$-$C_{20}$ cycloaliphatic, $C_2$-$C_{20}$ heterocycloaliphatic, $C_6$-$C_{20}$ aryl, and $C_2$-$C_{20}$ heteroaryl.

3. The method of claim 1 wherein Z is selected from the group consisting of $C_2$-$C_{20}$ heterocycloaliphatic, and $C_2$-$C_{20}$ heteroaryl.

4. The method of claim 1 wherein Z is selected from the group consisting of tetrahydrofuranyl, tetrahydrothiophenyl, and tetrahydropyrrolyl.

5. The method of claim 1 wherein Z is 2-tetrahydrofuranyl.

6. The method of claim 1 wherein Z is 2-tetrahydrofuranyl and C2 on the tetrahydrofuran ring has the (S) stereochemical configuration.

7. The method of claim 1 wherein $R^{11}$ is $C_1$-$C_{20}$ aliphatic.

8. The method of claim 1 wherein $R^{11}$ is tertiary-butyl.

9. The method of claim 1 wherein $R^{12}$ is selected from the group consisting of $C_1$-$C_{20}$ aliphatic, $C_6$-$C_{20}$ aryl, $C_2$-$C_{20}$ heteroaryl, and combinations thereof.

10. The method of claim 1 wherein $R^{12}$ is para-nitrobenzyl.

11. The method of claim 1 wherein $R^{13}$ is selected from the group consisting of $C_1$-$C_{20}$ aliphatic, $C_6$-$C_{20}$ aryl, $C_2$-$C_{20}$ heteroaryl, and combinations thereof.

12. The method of claim 1 wherein $R^{13}$ is benzyl.

* * * * *